United States Patent
Gross (10) Patent No.: US 9,668,749 B2
(45) Date of Patent: Jun. 6, 2017

(54) ADJUSTABLE REVISION GUIDE

(71) Applicant: MICROPORT ORTHOPEDICS HOLDINGS INC., Tiel (NL)

(72) Inventor: Michael Gross, Halifax (CA)

(73) Assignee: MicroPort Orthopedic Holdings Inc., Tiel (NL)

( * ) Notice: Subject to any disclaimer, the term of this patent is extended or adjusted under 35 U.S.C. 154(b) by 0 days.

(21) Appl. No.: 14/828,073

(22) Filed: Aug. 17, 2015

(65) Prior Publication Data

US 2016/0183952 A1 Jun. 30, 2016

Related U.S. Application Data

(63) Continuation of application No. 14/216,193, filed on Mar. 17, 2014, now Pat. No. 9,138,248, which is a continuation of application No. 13/793,744, filed on Mar. 11, 2013, now Pat. No. 8,828,014, which is a continuation of application No. 12/942,186, filed on Nov. 9, 2010, now Pat. No. 8,403,935.

(60) Provisional application No. 61/259,780, filed on Nov. 10, 2009, provisional application No. 61/260,794, filed on Nov. 12, 2009.

(51) Int. Cl.
| | | |
|---|---|---|
| A61B 17/15 | (2006.01) | |
| A61B 17/72 | (2006.01) | |
| A61B 17/17 | (2006.01) | |
| A61F 2/46  | (2006.01) | |

(52) U.S. Cl.
CPC ........ *A61B 17/155* (2013.01); *A61B 17/1764* (2013.01); *A61B 17/72* (2013.01); *A61F 2/4684* (2013.01)

(58) Field of Classification Search
CPC .......................... A61B 17/72; A61B 17/1764
See application file for complete search history.

*Primary Examiner* — Andrew Yang
(74) *Attorney, Agent, or Firm* — Adams and Reese LLP (57) ABSTRACT

An axial height adjustable, revision cutting in the shape of a final distal femur implant component. The revision guide includes a rod adapted for intimate contact within an intramedullary canal of a femur, and includes a threaded passageway. The revision cutting guide is adapted for removable attachment to a distal portion of the femur. A vernier-bolt is rotatably positioned through the shaped body of the revision cutting guide so as to be adjustably received within the threaded passageway thereby providing for movement of the shaped body of the revision cutting guide relative to the distal portion of the femur.

11 Claims, 11 Drawing Sheets

ADJUSTABLE REVISION GUIDE

This application is a continuation of U.S. patent application Ser. No. 14/216,193, filed Mar. 17, 2014, which is a continuation of U.S. patent application Ser. No. 13/793,744, filed Mar. 11, 2013, which is a continuation of U.S. patent application Ser. No. 12/942,186, which was filed Nov. 9, 2010 claiming priority to U.S. Provisional Patent Application Ser. No. 61/259,780, filed Nov. 10, 2009, entitled "Adjustable Revision Guide" and to U.S. Provisional Patent Application Ser. No. 61/260,794, filed Nov. 12, 2009, entitled "Adjustable Revision Guide," the entireties of which are incorporated by reference herein.

FIELD OF THE INVENTION

The present invention relates to surgical guides for revising the distal femur of a patient undergoing total knee replacement therapy.

BACKGROUND OF THE INVENTION

Total knee replacement prostheses are known in the art. In many instances, a specially designed jig or fixture enables the surgeon to make accurate and precise bone resections of the femoral surface in order to accept such prostheses. The ultimate goal with any total knee prosthesis is to approximate the function of the natural, healthy structures that the prosthesis is replacing. Should the prosthesis not be properly attached to the femur any misalignment could result in discomfort to the patient, gate problems, or degradation of the prosthesis.

For example, when attaching a knee prosthesis it is desirable to orient the prosthesis such that the pivot axis of the knee joint lies within a transverse plane that is generally oriented perpendicular to the mechanical axis of the femur. The mechanical axis lies along a line which intersects the femoral head and the center of the ankle. In the prior art, the mechanical axis had been determined from an inspection of a radiograph of the femur to be resected prior to, or even during the surgery. During the actual operation, the mechanical axis is determined by computing its valgus angle from the femoral shaft axis. It is then necessary to manually align any cutting guide and its fixtures with respect to the femoral shaft axis in order to achieve an optimum cut.

Often such cutting guides include a femoral intramedullary stem which is inserted through a pre-drilled passage way formed in the intercondylar notch and upwardly through the femur along the femoral shaft axis. Such femoral intramedullary stems often include a bracket which supports the distal femur cutting guide. The bracket includes a first pin which extends through the cutting guide to act as a pivot axis. A second pin is attached to the bracket so as to extend through an arcuate slot in the cutting guide. The cutting guide included pairs of opposing slots formed along its sides which are oriented so as to be perpendicular to a central axis of symmetry of the cutting guide. When the cutting guide is pivoted, such that the central axis of symmetry lay along the mechanical axis, so as to form the appropriate angle with the femoral shaft axis, the cutting guide slots are positioned to be perpendicular to the mechanical axis. The cutting guide is then locked into the predetermined angle with the femoral shaft axis, and resection of the distal femur may proceed.

Many examples of devices and methods may be found in the art for preparing the distal femur for total knee arthroplasty, such as U.S. Pat. No. 7,172,597 which discloses a provisional component for use with differently sized first and second prosthetic orthopedic components. The provisional component has a configuration that is substantially similar to the first prosthetic component and has a predefined correspondence to the second prosthetic component. The provisional component is mounted on a bone to assess the fit of the first prosthetic component. The provisional component includes a referencing element for defining a reference point on the bone if the fit of the provisional component indicates that the second prosthetic component should be used. An instrument guide is aligned with the reference point and used to properly position a surgical instrument to prepare the bone to receive the second prosthetic component. The provisional and prosthetic components may all be femoral components which have an articulating surface defining a single condylar-shaped projection.

U.S. Pat. No. RE39,301, incorporated herein by reference, discloses a method and apparatus for knee replacement surgery in which a femoral provisional component is provided which corresponds to a permanent component to be implanted in a human. It includes structures suitable for establishing the correct fit and position of such a component, prior to its implantation, in relation to the soft tissues of the knee before final resection of the anterior femoral surface. The provisional component further includes a cutting guide for anterior surface resection such that accurate cuts may be made with the provisional component in place. The method involves preparing the distal femoral surface using the femoral intramedullary canal as a constant reference point for posterior and distal cutting guides followed by locating the provisional component by means of a provisional intramedullary stem so that the relationship with the soft tissues of the knee may be accurately established.

U.S. Pat. No. 6,187,010, incorporated herein by reference, discloses bone cutting guides that appear to enable a surgeon to better gauge required resection characteristics. At least a portion of the guide is transparent, thereby enabling the user to optimize cut estimates and to visualize the resection as it is being performed. At least a portion of the outer surface of the body is shaped to interact with another bone or prosthetic element associated with a joint, thereby enabling the device to function both as a trial and as a cutting guide.

U.S. Pat. No. 5,879,393 discloses a posterior stabilized femoral trial apparatus for preparing a patient's femur to receive a posterior stabilized femoral prosthesis. The device includes a trial body with proximal and distal portions, the distal portion having an articulating surface for articulating with a patient's tibial component. A module selected from a kit fits the trial body at the proximal surface. The module includes a rasping surface that extends longitudinally. The trial body includes cutting surfaces at the posterior condyles. The module is removably attachable to the trial body at the proximal surface. During use the surgeon may resect the patient's femur in a revision case using the trial.

U.S. Pat. No. 6,575,980 discloses an instrument for shaping a femur preparatory to implantation of a knee prosthesis. A gap checking device is fixed to the distal end of the patient's femur and referenced to the epicondyles of the femur. The gap checking device includes slots through which a cutting instrument can be passed to shape the femur so that it can receive the femoral component of the prosthesis. One of the slots enables the distal femoral cut to be made. The thickness of the gap checking device is selected so that the distance between the distal femoral cut and the distal surface of the gap checking device plus the thickness of a shim resting on the cut proximal tibia surface is equal to the combined thickness of the tibial and femoral components of the prosthesis. This arrangement apparently enables balancing of the ligaments to be checked before the femoral cuts are made, but while the gap checking device is secured to the femur.

U.S. Pat. No. 5,053,037 discloses femoral instrumentation for long stem surgery, and provides a femoral drill guide with interchangeable femoral collets, a femoral reamer, and a femoral anterior/posterior cutting block with an adaptable anterior femoral ledge. This instrumentation allows all cuts to be made relative to the long stem component of a femoral prosthesis which will fit in the hole formed by the reamer with the collet and cutting block both oriented on the reamer, and all cuts made by the surgeon will be oriented relative to the long stem or spike component of the femoral prosthesis.

With many of the foregoing, except U.S. Pat. No. 6,187,010, it would be common practice to make one or more cuts with a resection guide in place, then move the guide aside in order to view the interface, to ensure that sufficient bone has been removed to facilitate the most ideal cement interface between the resected bone and implant component. This trial-and-error process not only consumes valuable time during the operation, but may lead to the removal of more bone stock than necessary to achieve fixation. During revision arthroplasty, such trial-and-error is complicated owing to the increased number of resected surfaces involved, and the need to ensure that these surfaces and the medullary stem are all properly aligned during the testing of trial implants and the attachment of the final prosthetic device. In the event of a misalignment, the surgeon may choose to use a final implant having a smaller than optimal diameter stem, for example, to take up the slack upon discovering a slight misalignment with respect to the stem and the resected surfaces. As such, none of the forgoing methods or devices have adequately provided surgeons with a way to easily locate resection guides in relation to the patient's body during orthopedic procedures, such as, total knee replacement surgery.

SUMMARY OF THE INVENTION

The present invention provides an axial height adjustable, revision cutting guide in the shape of a final distal femur implant component. In one embodiment, the revision guide includes a rod adapted for intimate contact within an intramedullary canal of a femur following preparation of the canal to receive the rod. The rod includes a threaded passageway extending longitudinally from a distal end, which is accessible when the rod is installed within the canal. A shaped body of the revision cutting guide is adapted for removable attachment to a distal portion of the femur, and includes an outer surface configured to co-act in a joint and at least two bone-cutting guides are defined through the body corresponding to a level of bone resection A vernier-bolt is rotatably positioned through the shaped body of the revision cutting guide so as to be adjustably received within the threaded passageway thereby providing for movement of the shaped body of the revision cutting guide relative to the distal portion of the femur.

In another embodiment, a method is provided for implanting a condylar prosthesis onto the proximal aspect of a femur. A trial implant is first provided, in combination with a rod adapted for intimate contact within an intramedullary canal of a femur following preparation of the canal to receive the rod. The rod includes a threaded passageway extending longitudinally from a distal end, which is accessible when the rod is installed within the canal. A trial implant body is adapted for removable attachment to a distal portion of the femur. The trial implant body includes an outer surface configured to co-act in a joint and at least two bone-cutting guides are defined through the trial implant body corresponding to a level of bone resection. A vernier-bolt is rotatably positioned through the trial implant body so as to be adjustably received within the threaded passageway. The trial implant body is positioned on the distal aspect of the femur such that the vernier-bolt is threadingly received within the threaded passageway. By then rotating the vernier-bolt so as to move the trial implant body relative to the distal aspect of the femur, adjustments may be made to the position of the trial implant relative to the femur A shaping tool is positioned with one of at least two bone-cutting guides, and then moved along one of the at least two bone-cutting guides so as to resect a selected portion of the femur exposed through the opening. A trial reduction of the knee joint is performed while the trial implant body remains seated on the distal aspect of the femur.

In another embodiment, an adjustable trial/cutting guide is provided for use in conjunction with knee joint-revision surgery. An intramedullary rod is provided that is adapted for intimate contact within an intramedullary passageway of a femur following preparation of the passageway to receive the intramedullary rod. The intramedullary rod includes a finely threaded passageway extending longitudinally from a distal end, which is accessible when the rod is installed within the passageway. An adjustable trial/cutting guide is adapted for removable attachment to a distal portion of the femur. The adjustable trial/cutting guide includes an outer surface defining an intercondylar notch configured to co-act in a joint and at least two bone-cutting guides defined through the adjustable trial/cutting guide corresponding to a level of bone resection. A vernier-bolt is rotatably positioned through the intercondylar notch so as to be operably and adjustably received within the threaded passageway thereby providing for movement of the adjustable trial/cutting guide relative to the distal portion of the femur to thereby locate the at least two bone-cutting guides for resection of the femur.

BRIEF DESCRIPTION OF THE DRAWINGS

These and other features and advantages of the present invention will be more fully disclosed in, or rendered obvious by, the following detailed description of the preferred embodiments of the invention, which are to be considered together with the accompanying drawings wherein like numbers refer to like parts and further wherein.

DETAILED DESCRIPTION OF THE PREFERRED EMBODIMENT

This description of preferred embodiments is intended to be read in connection with the accompanying drawings, which are to be considered part of the entire written description of this invention. The drawing figures are not necessarily to scale and certain features of the invention may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. The term "operatively connected" is such an attachment, coupling or connection that allows the pertinent structures to operate as intended by virtue of that relationship. In the claims, means-plus-function clauses, if used or implied, are intended to cover the structures described, suggested, or rendered obvious by the written description or drawings for performing the recited function, including not only structural equivalents but also equivalent structures.

The present invention solves many of the problems in the art by providing an axial height adjustable, revision cutting guide in the shape of a final distal femur implant component, thereby ensuring that once the guide is removed, the final implant component will inherently match the executed resections, thereby saving considerable time while improving accuracy. Referring to FIGS. 1-5, an adjustable trial/cutting guide 5 formed in accordance with one embodiment of the invention is similar to that employed in most knee prosthetics in that it comprises an anterior flange 8, a pair of posterior condylar flanges 10 and 12, and a distal femur contacting surface 14. A distal joint surface 16 corresponds to the natural distal femoral surface of the human knee including condylar surfaces 19 and 21 for cooperation with the corresponding end of a tibia (not shown). Structures for patellar tracking along the arc of the joint surface of the anterior flange 8 and between the distal condylar surfaces 19 and 21 is also provided on adjustable trial/cutting guide 5.

Figure 1:
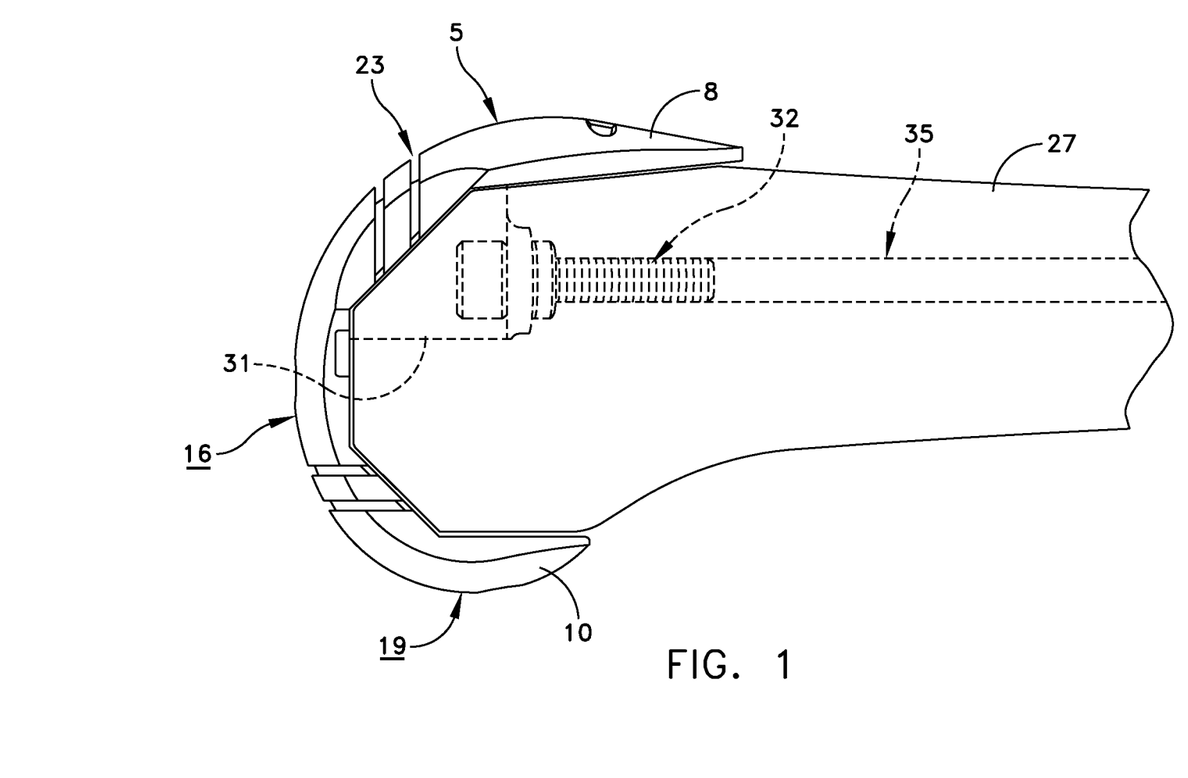
FIG. 1 is a side elevational view, partially in phantom, of an adjustable trial/cutting guide formed in accordance with one embodiment of the present invention, illustrated to reflect completed assembled to a distal portion of a femur.
Figure 2:
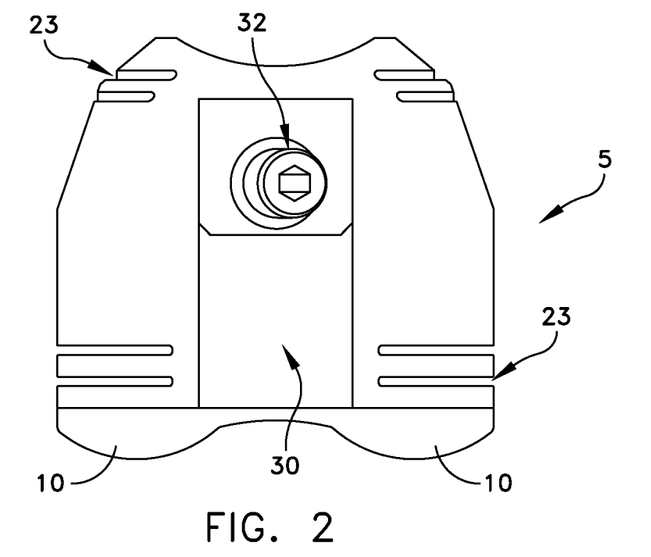
FIG. 2 is a front elevational view of the adjustable trial/cutting guide shown in FIG. 1.
Figure 3:
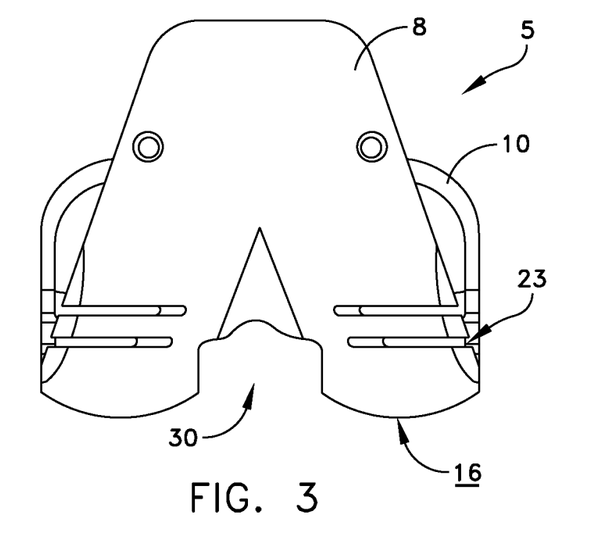
FIG. 3 is a perspective front view of the adjustable trial/cutting guide shown in FIGS. 1 and 2.
Figure 4:
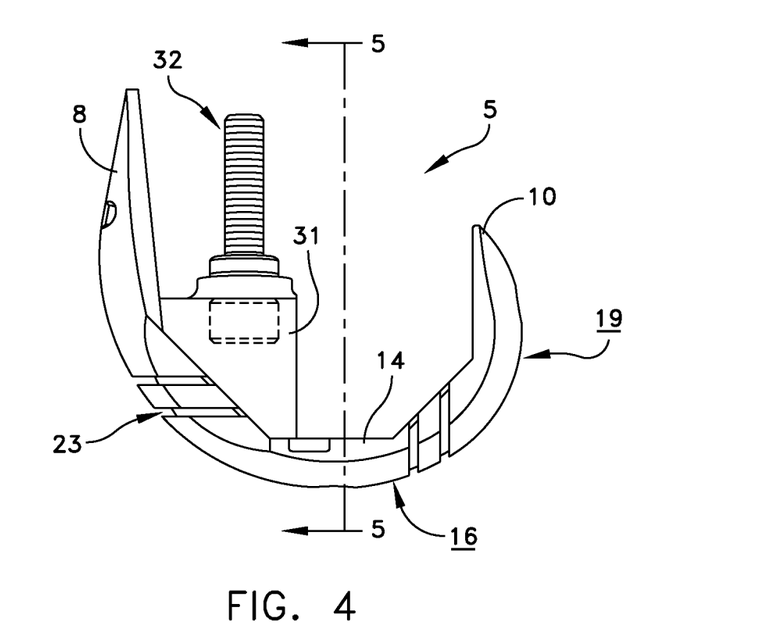
FIG. 4 is a side elevational view of the adjustable trial/cutting guide formed in accordance with the present invention.
Figure 5:
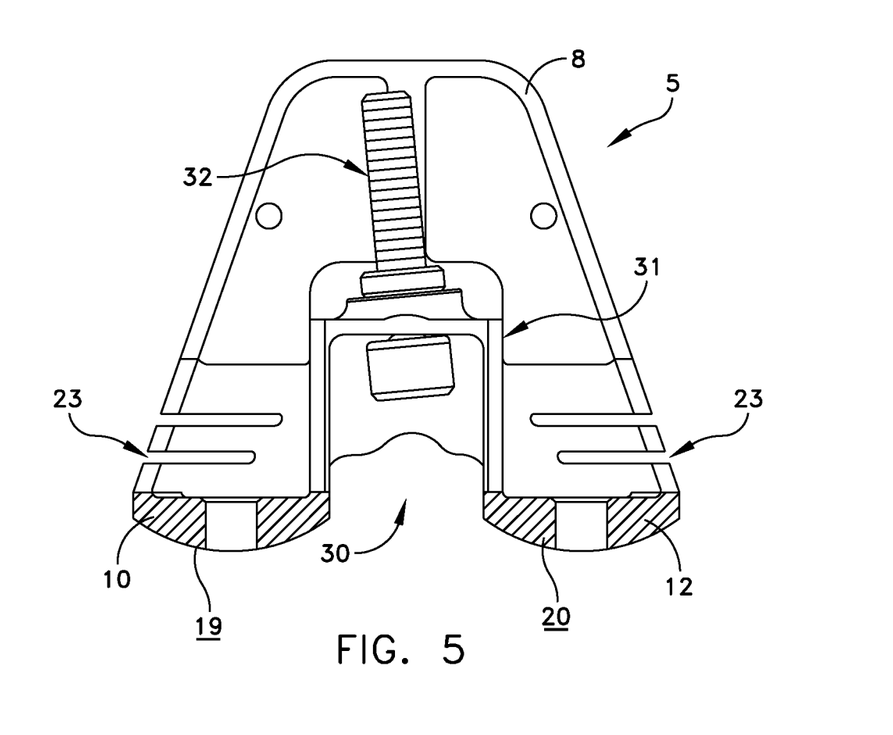
FIG. 5 is a partially sectioned view of the adjustable trial/cutting guide, as taken along line 5-5 in FIG. 4.
Figure 6:
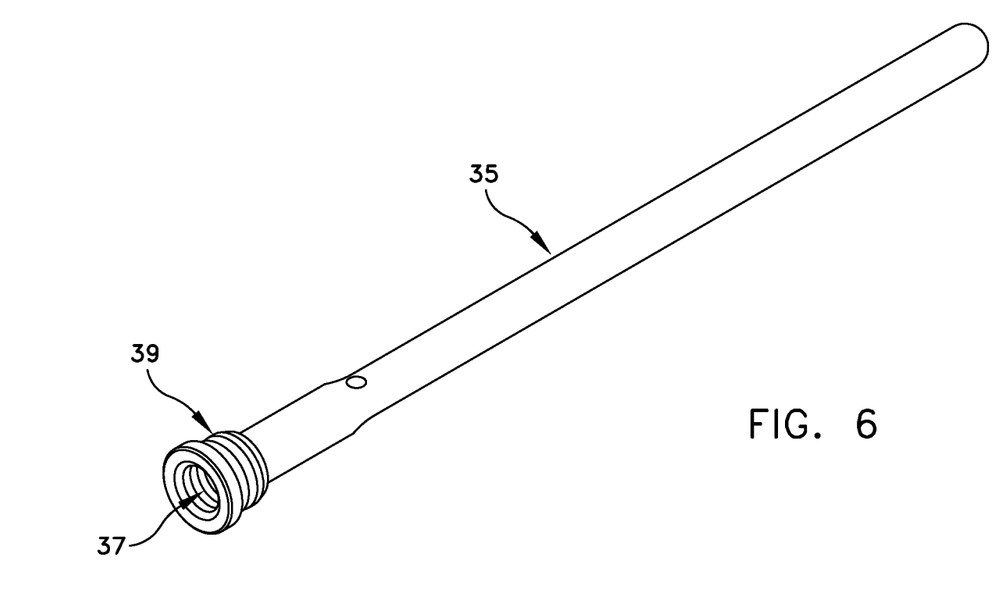
FIG. 6 is a perspective view of an intramedullary rod configured to be used in combination with an adjustable trial/cutting guide in accordance with some embodiments.
Figure 7:
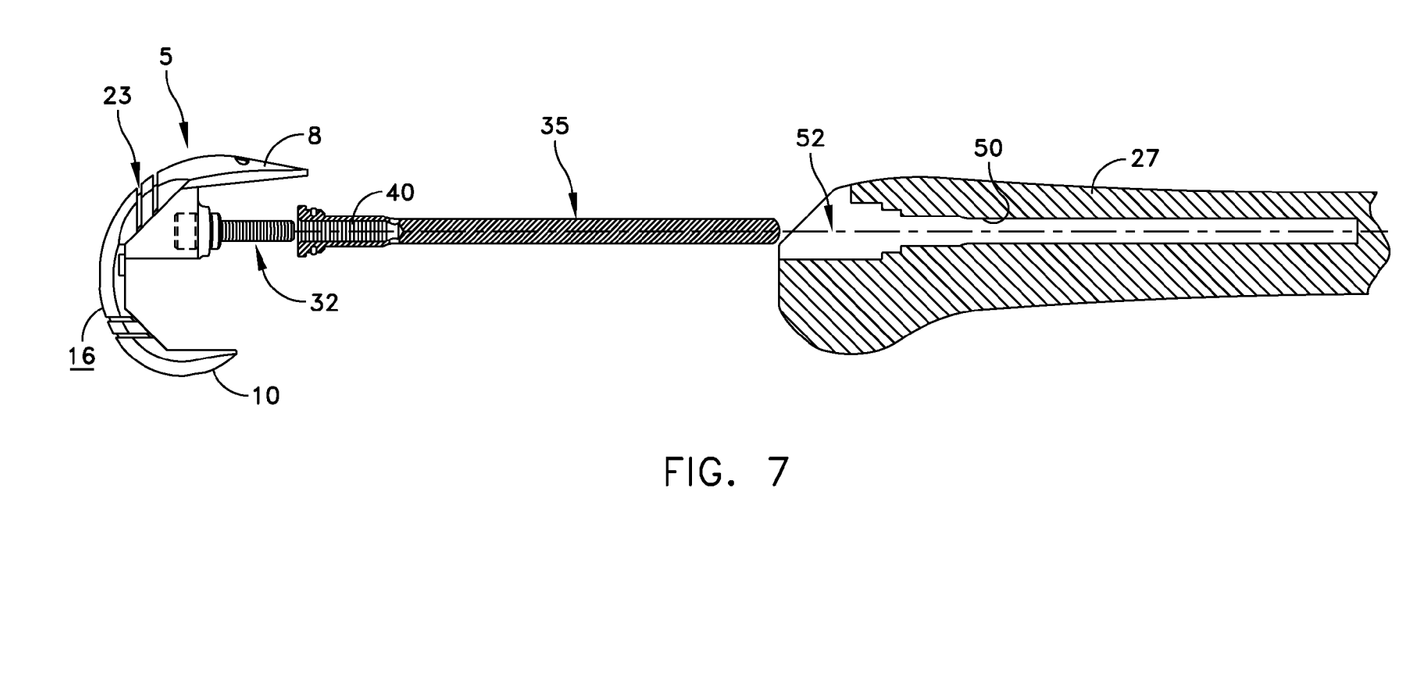
FIG. 7 is a partially cross-sectional view of one example of an adjustable trial/cutting guide being positioned for coupling to the femur in accordance with some embodiments.
Figure 11:
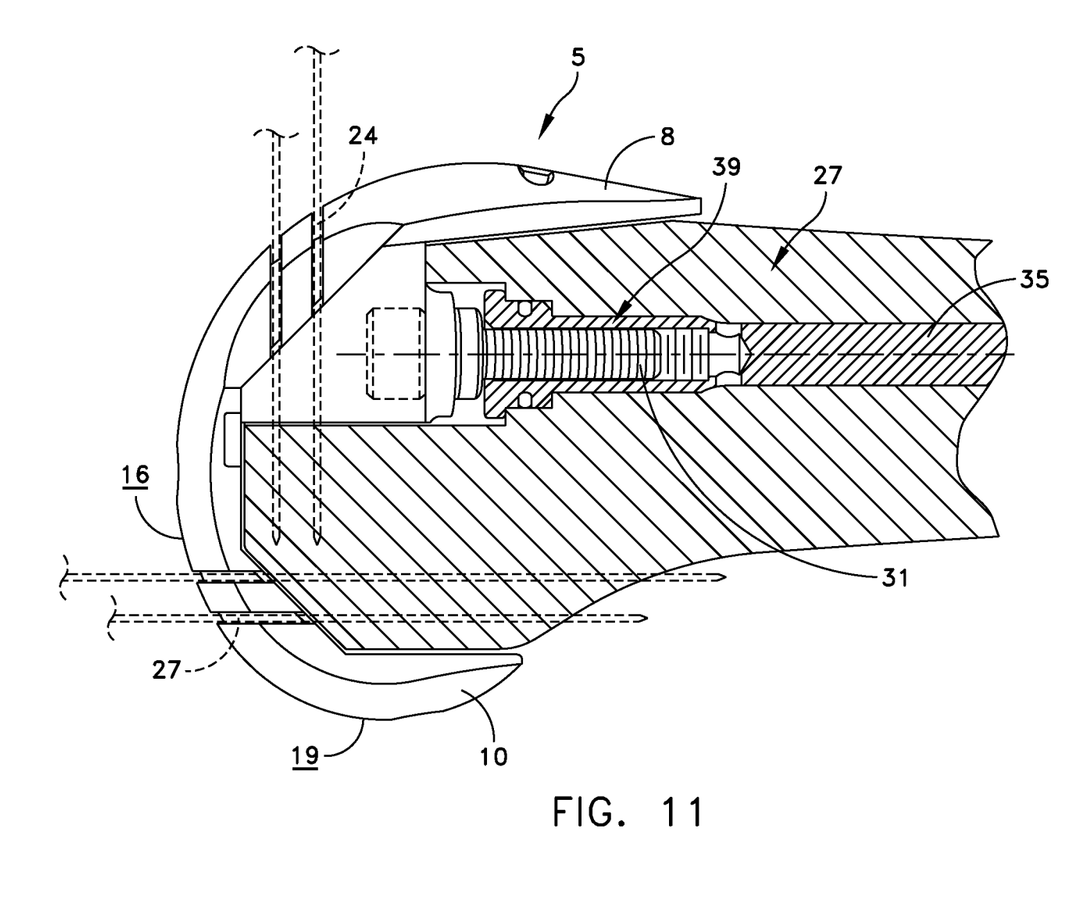
FIG. 11 is a partially cross-sectioned view, similar to FIGS. 7-10 showing adjustable trial/cutting guide located on the distal end of the femur, as adjusted by the vernier bolt, with phantom saw blades illustrated to show possible resection options available to the surgeon.

One or more guide slots 23 are defined in portions of anterior flange 8 and posterior condylar flanges 10 and 12 that are sized and oriented to accept corresponding saw blades 24 (FIG. 11) to allow for resection of bone while adjustable trial/cutting guide 5 is positioned on distal femur 27. Instead of including an intramedullary locating shaft on distal femur contacting surface 14, the present invention defines a precisely threaded through-bore 29 within an anterior notch 30 formed in adjustable trial/cutting guide 5. A corresponding protrusion 31 projects outwardly from distal femur contacting surface 14 between posterior condylar flanges 10 and 12 (FIGS. 1, 4, and 5). Through-bore 29 communicates between surface 16 of anterior flange 8 and distal femur contacting surface 14, and accepts a complementarily threaded vernier-bolt 32. Vernier-bolt 32 provides for fine adjustments to the position of adjustable trial/cutting guide 5 relative to distal femur 27 during the trial phase of total knee replacement surgery, as will be more fully disclosed in detail below. An intramedullary rod 35 (FIG. 6) is used in combination with adjustable trial/cutting guide 5, and has a blind bore 37 defined at its distal most end 39. The interior wall of intramedullary rod 35, that defines blind bore 37, includes a fine thread 40 that is complementary to the fine thread, i.e., an accurate and precise helical thread, defined on the outer surface of vernier-bolt 32.

Figure 12:
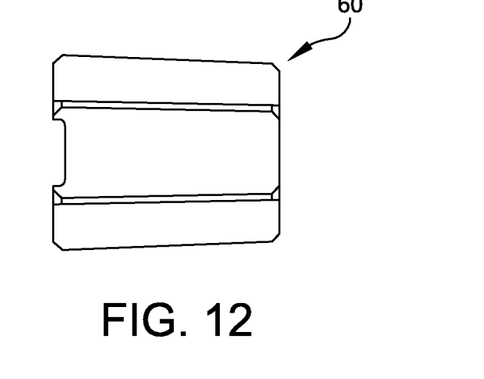
FIG. 12 is a side elevational view of a bushing that may coupled to an end of the intramedullary rod shown in FIG. 8a used as a spacer.
Figure 13:
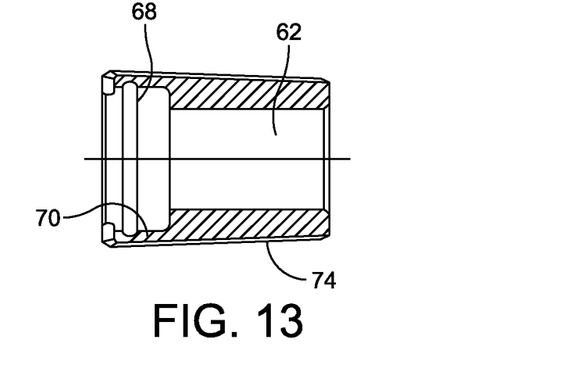
FIG. 13 is a sectional view of the bushing shown in FIG. 12 taken along line A-A in FIG. 12.
Figure 14:
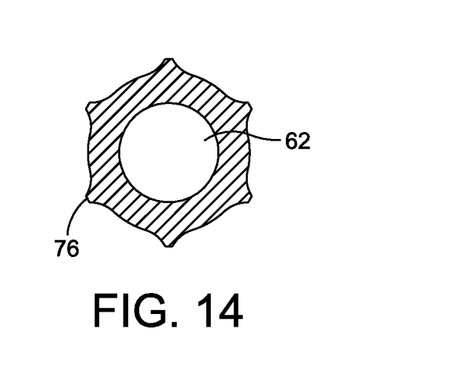
FIG. 14 is a sectional view of the bushing shown in FIG. 12 taken along line B-B in FIG. 12.
Figure 15:
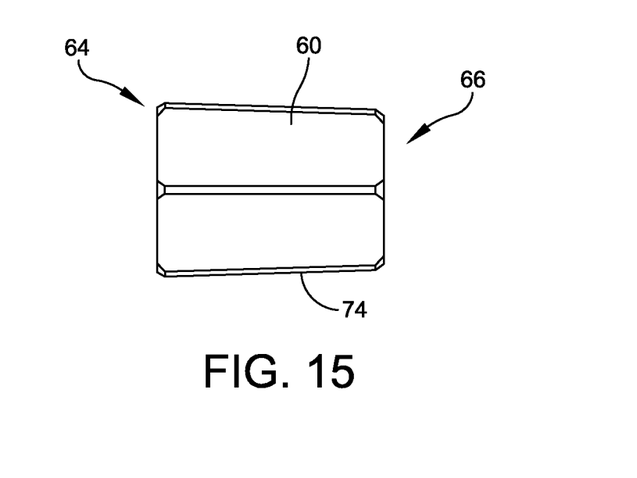
FIG. 15 is another side elevational view of a bushing.

FIGS. 12-15 illustrate one example of a tapered bushing 60 that may be coupled to the distal end of the intramedullary rod 35. As best seen in FIG. 13, the bushing 60 defines a through hole 62 having a first diameter D1. A proximal end 64 of the bushing 60 may define an opening having a diameter D2 that is larger than the diameter D1 defined by the distal end 66 of bushing 60. A groove 68 may be formed on an interior surface 70 of proximal end 64 of bushing 60. One or more fins 72 may extend along a length an exterior surface 74 of bushing 60 as best seen in FIGS. 12, 14, and 15. The longitudinal fins 76 work as an anti-rotational feature to prevent bushing 60 from rotating when installed in an intramedullary cavity as described below. Bushing 60 may be provided in a variety of sizes as will be understood by one skilled in the art. Example sizes of bushing 60 include, but are not limited to, 16 mm, 18 mm, 20 mm, 22 mm, and 24 mm.

During a total knee replacement procedure, the present invention provides a trial component that offers the surgeon the possibility to perform flexion trials, as well as, resection procedures without the need to remove the trial prosthesis from the distal femur. The structural arrangement of adjustable trial/cutting guide 5 enables it to be placed in the joint space following initial resection of the distal and posterior femur. Preferably, the resection of the posterior and distal surfaces of the medial and lateral condyles is kept to the least amount necessary. In addition, each condyle is preferably resected independently of the other and separate augments are selected for test fitting adjustable trial/cutting guide 5 and for implantation of the final femoral implant component. These initial cuts may be standardized for a typical range of knee sizes or the cuts may be made on an individual basis according to the needs of the particular patient. The function of the patient's knee may be checked as well as the relationship of adjustable trial/cutting guide 5 to the soft tissues of the joint. Although the correct size adjustable trial/cutting guide 5 and, thereby, the prosthesis will usually be determined before surgery, it may be necessary, following initial resection, to adjust to an alternative size component in order to tighten the flexion and extension gaps. The present invention facilitates this process by permitting the sizes to be tested and the distal femur to be further resected, as needed, before the final prosthesis is implanted.

Figure 8:
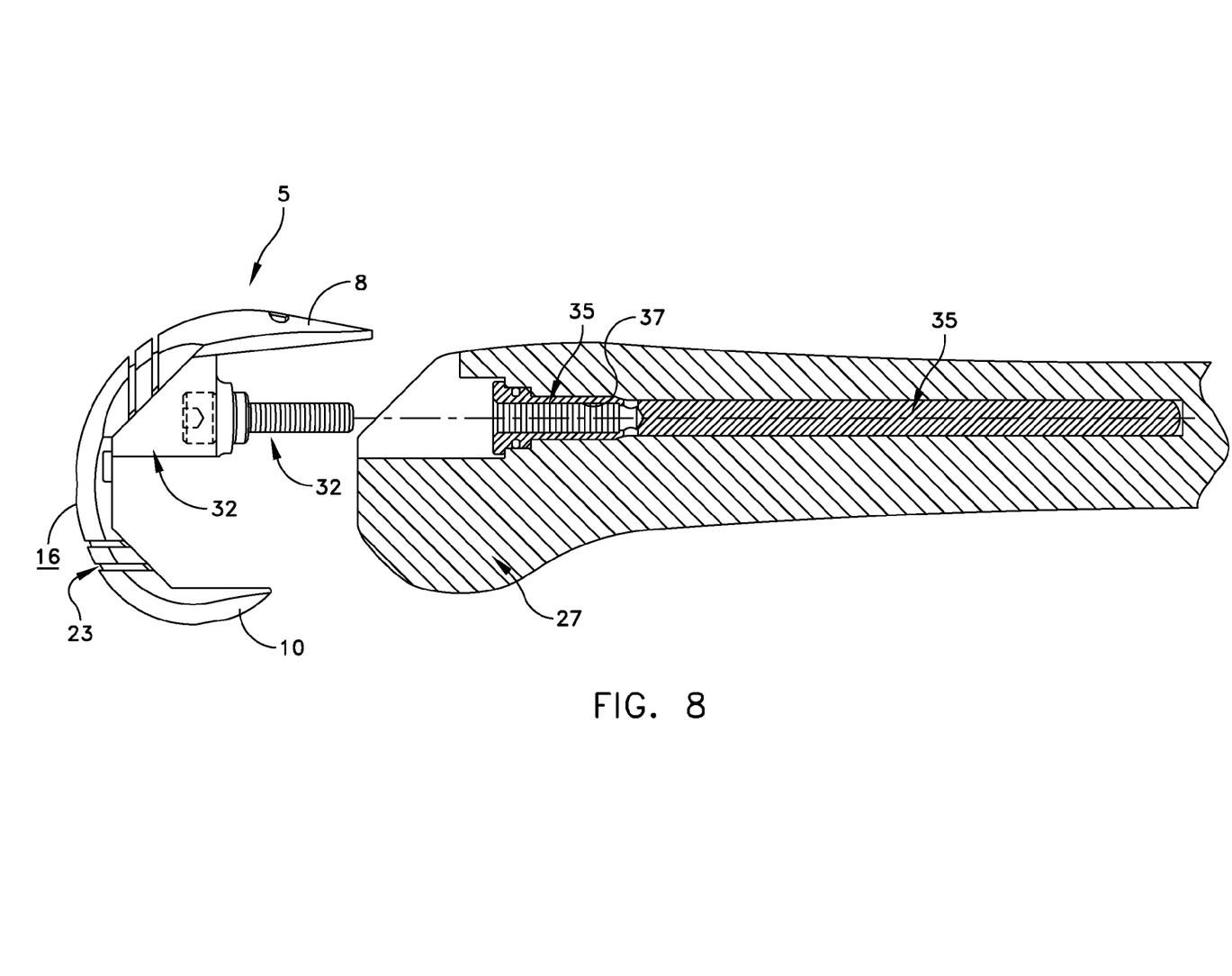
FIG. 8 is similar to FIG. 7, but with an intramedullary rod positioned within a longitudinal canal formed within the femur.
Figure 8A:
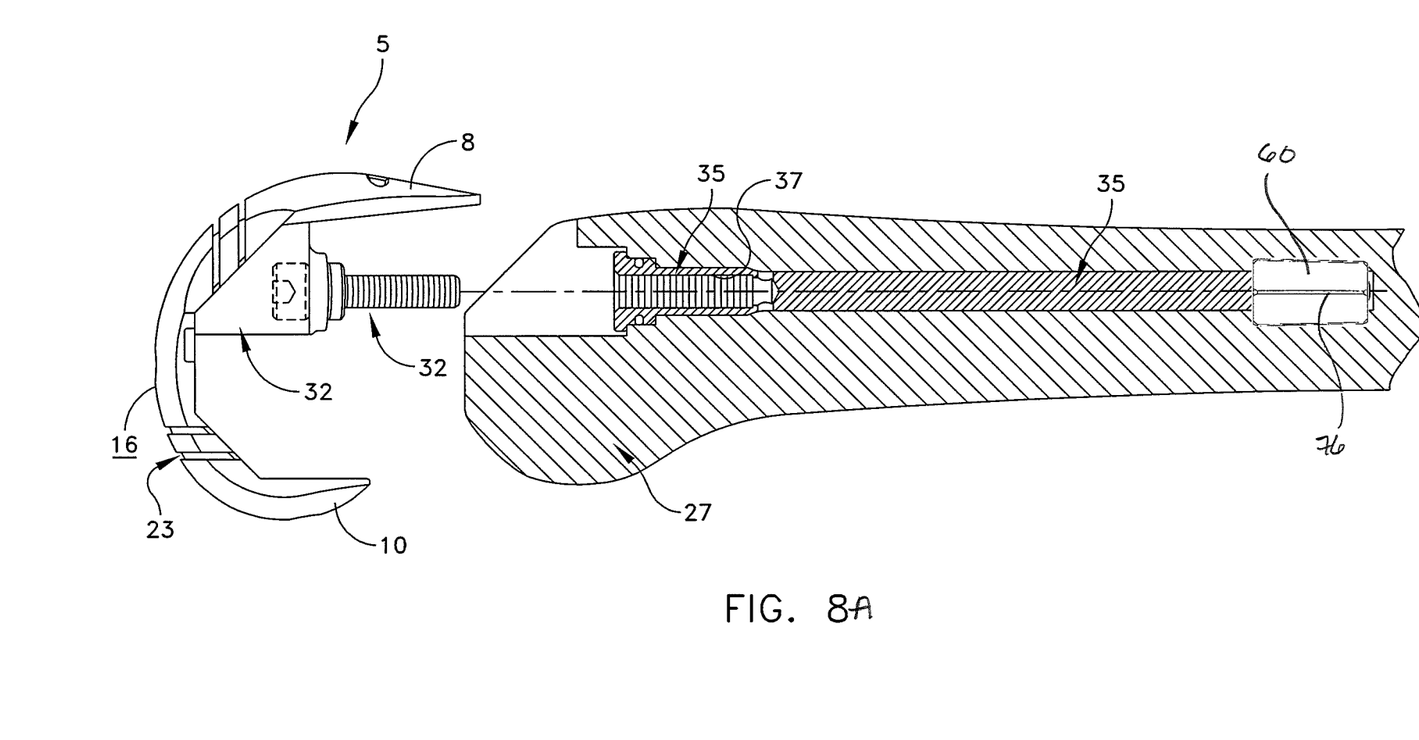
FIG. 8a is similar to FIG. 8, but with a bushing disposed on a distal end of the intramedullary rod positioned within the longitudinal canal.

Referring to FIGS. 1 and 7-11, intramedullary rod 35 is first located within a longitudinally extending a pre-drilled canal 50 formed in the intercondylar notch and upwardly through the femur along the femoral shaft axis. A mouth 52 is defined at the distal most end of femur 27, and is sized to receive protrusion 31 projecting outwardly from distal femur contacting surface 14 between posterior condylar flanges 10 and 12 of adjustable trial/cutting guide 5. With intramedullary rod 35 located within a longitudinally extending canal 50 (FIG. 8) adjustable trial/cutting guide 5 is assembled to distal femur 27 by arranging vernier-bolt 32 in coaxially aligned, spaced relation to blind bore 37 defined at distal most end 39 of intramedullary rod 35. In revision surgical procedures, bushing 60 may be disposed at the distal end of the intramedullary rod 35 to fill space that may have formed around an old implant as shown in FIG. 8a. Providing bushing 60 in various sizes as described above enables a surgeon to select an appropriate size depending on the condition of the intramedullary cavity. The tapered lengthwise fins 76 prevent rotation of the intramedullary rod 35.

Figure 9:
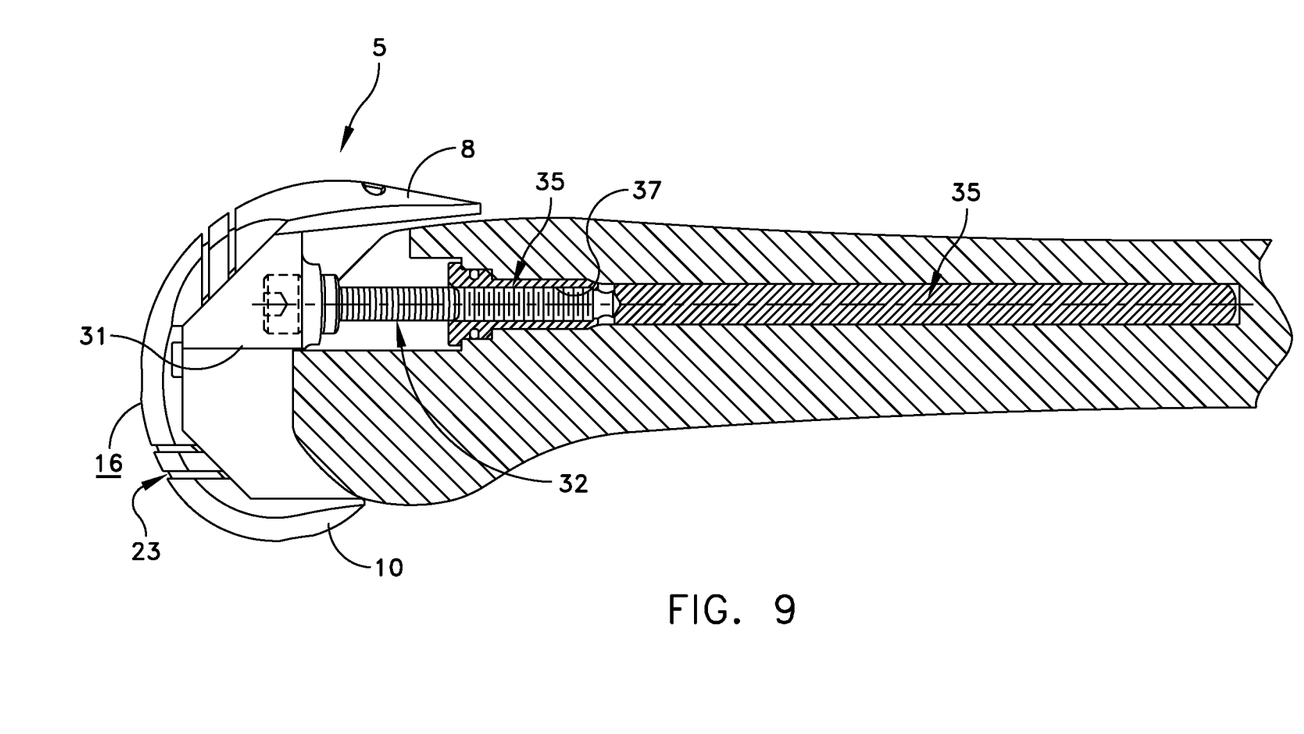
FIG. 9 is similar to FIG. 8, but showing an initial engagement of a vernier bolt with a distal portion of the intramedullary rod so as allow controlled movement of adjustable trial/cutting guide toward or away from the distal end of the femur.
Figure 10:
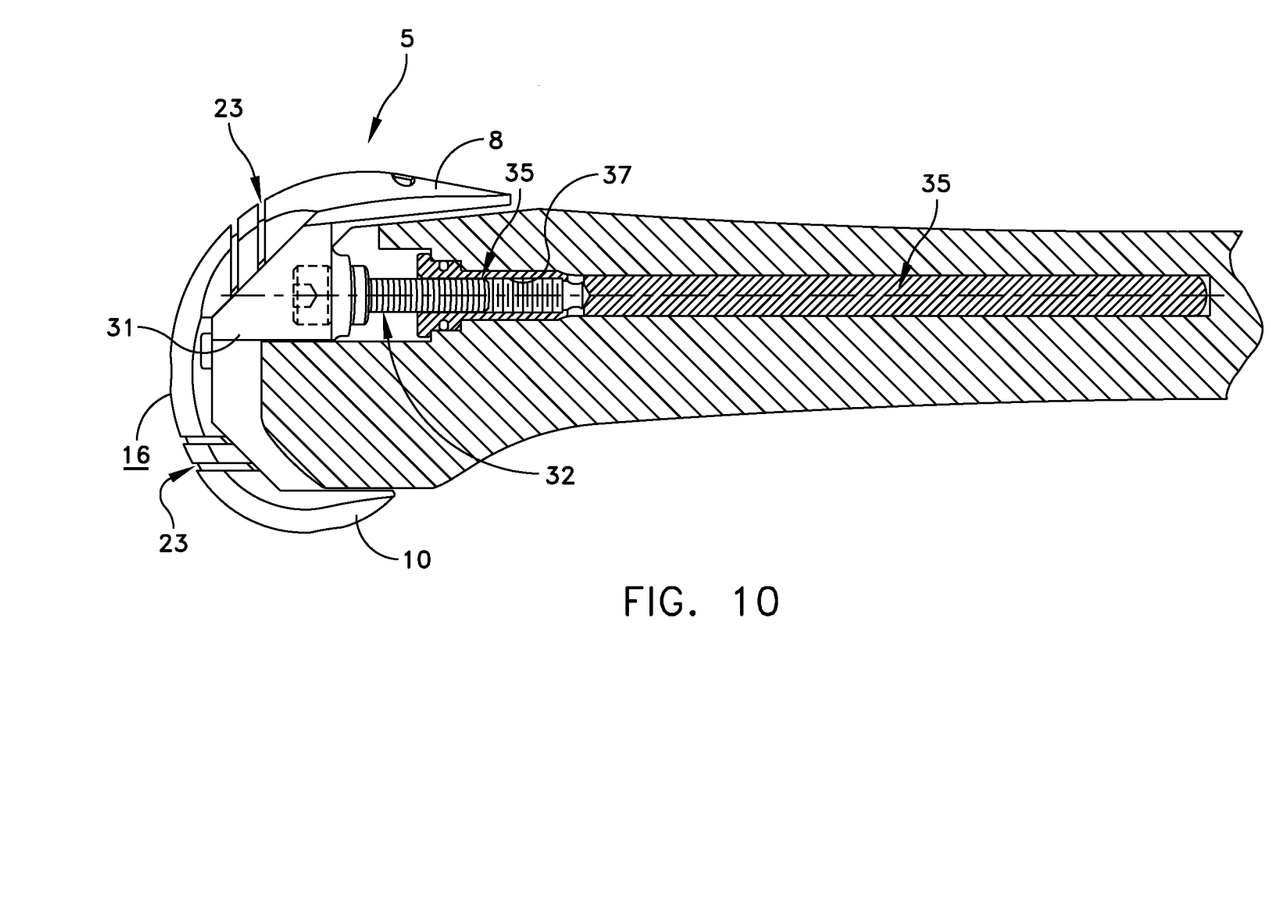
FIG. 10 is similar to FIG. 9, but showing a further longitudinal adjustment of the adjustable trial/cutting guide on the distal end of the femoral bone.

Once in this position, adjustable trial/cutting guide 5 is moved toward intramedullary rod 35 such that the free end of vernier-bolt 32 enter blind bore 37 so as to threadingly engage fine thread 40 (FIG. 9). Adjustable trial/cutting guide 5 may then be move toward or away from distal femur 27, parallel with the mechanical axis of femur 27, by clockwise or counter clockwise rotation of vernier-bolt 32. As a result of the finely threaded, complementary threads of vernier-bolt 32 and thread 40, small longitudinal adjustments may be made in the position of adjustable trial/cutting guide 5 relative to femur 27. In this way, trial flexions and extensions of the joint may be made, with adjustments to the axial position of adjustable trial/cutting guide 5 on distal femur 27 being made via engagement of vernier-bolt 32 with intramedullary rod 35.

Once correct working of the joint is established, including balancing of the soft tissues, anterior chamfer and anterior flange resection may be accomplished through cutting guides 23 (FIG. 11) without need for removing adjustable trial/cutting guide 5 thereby ensuring that these cuts are made in the correct locations relative to the intramedullary canal and at the correct angles relative to the intramedullary stem. Because the system of revision for which adjustable trial/cutting guide 5 is intended uses the intramedullary canal of the femur as a reference point, the angle established between the intramedullary shaft and the anterior flange of an implant is constant through all sizes of such implants.

It is to be understood that the present invention is by no means limited only to the particular constructions herein disclosed and shown in the drawings, but also comprises any modifications or equivalents within the scope of the claims.

What is claimed is:

1. An adjustable knee revision guide apparatus, comprising:
   a rod sized and configured to be received within an intramedullary canal formed in a femur, the rod defining a passageway extending longitudinally from a distal end of the rod, and the passageway being at least partially threaded with a fine thread;
   a body including an outer surface configured to act as a knee joint, a distal femur contacting portion configured to be attached removably to a distal portion of the femur, at least one pair of coinciding lateral and medial distal resection slots formed through a distal anterior portion of the body for use in making a distal resection, the lateral distal resection slot formed along a lateral edge of the body and the medial distal resection slot formed along a medial edge of the body, a pair of posterior condylar flanges forming a distal femur contact surface, at least one pair of coinciding lateral and medial posterior resection slots formed through a distal posterior portion of the body for use in making a posterior resection, the lateral posterior resection slot formed along the lateral edge of the body and the medial posterior resection slot formed along the medial edge of the body, and a threaded through bore defined within an anterior notch, the threaded through bore having a fine thread; and
   a bolt sized and configured to be positioned rotatably in the threaded through bore of the body and to be received within the passageway such that the bolt is adjustable and provides for movement of the body relative to the distal portion of the femur, the bolt having a fine thread configured to match the thread of the through bore of the body and the thread in the passageway of the rod to thereby facilitate accurate and precise adjustments between the body and the rod.

2. The apparatus of claim 1, wherein the body includes a protrusion that projects outwardly from the distal femur contacting portion between the pair of posterior condylar flanges.

3. The apparatus of claim 2, wherein the through bore communicates between the distal joint surface and the distal femur contacting portion.

4. The apparatus of claim 1, wherein the at least one pair of coinciding lateral and medial distal resection slots includes a second pair of coinciding lateral and medial distal resection slots, to thereby provide options for two distal resection locations.

5. The apparatus of claim 4, wherein the at least one pair of coinciding lateral and medial posterior resection slots includes a second pair of coinciding lateral and medial posterior resection slots, to thereby provide options for two posterior resection locations.

6. The apparatus of claim 1, further comprising the rod having a removable bushing coupled on a proximal end thereof.

7. The apparatus of claim 6, wherein the bushing is tapered.

8. The apparatus of claim 7, wherein the bushing is finned for anti-rotation.

9. The apparatus of claim 5, further comprising the rod having a removable bushing coupled on a proximal end thereof.

10. The apparatus of claim 9, wherein the bushing is tapered.

11. The apparatus of claim 10, wherein the bushing is finned for anti-rotation.

* * * * *